(12) United States Patent
Boskamp

(10) Patent No.: US 9,180,109 B2
(45) Date of Patent: Nov. 10, 2015

(54) USE OF GLYCERYL TRINITRATE FOR TREATING TRAUMATIC EDEMA

(75) Inventor: Marianne Boskamp, Bekmunde (DE)

(73) Assignee: G. POHL-BOSKAMP GMBH & CO. KG, Hohenlockstedt (DE)

( * ) Notice: Subject to any disclaimer, the term of this patent is extended or adjusted under 35 U.S.C. 154(b) by 0 days.

(21) Appl. No.: 13/813,676

(22) PCT Filed: Aug. 3, 2011

(86) PCT No.: PCT/EP2011/003890
§ 371 (c)(1),
(2), (4) Date: Feb. 1, 2013

(87) PCT Pub. No.: WO2012/016691
PCT Pub. Date: Feb. 9, 2012

(65) Prior Publication Data
US 2013/0129638 A1 May 23, 2013

(30) Foreign Application Priority Data
Aug. 3, 2010 (DE) .......................... 10 2010 033 182

(51) Int. Cl.
*A61K 31/21* (2006.01)
*A61K 9/00* (2006.01)

(52) U.S. Cl.
CPC ................ *A61K 31/21* (2013.01); *A61K 9/0014* (2013.01)

(58) Field of Classification Search
CPC ............. A61K 9/00; A61K 9/06; A61K 9/08; A61K 9/12; A61K 31/04; A61K 31/21; A61K 9/0014
USPC ....... 424/43, 45; 423/395; 436/117; 514/740, 514/742
See application file for complete search history.

(56) References Cited

U.S. PATENT DOCUMENTS

| | | | |
|---|---|---|---|
| 3,155,574 A * | 11/1964 | Silson et al. | 424/45 |
| 4,323,577 A | 4/1982 | Ohkuma et al. | |
| 4,542,013 A | 9/1985 | Keith | |
| 4,919,919 A * | 4/1990 | Aouda et al. | 424/45 |
| 5,186,925 A | 2/1993 | Cholcha | |
| 5,370,862 A | 12/1994 | Klokkers-Bethke et al. | |
| 5,698,589 A * | 12/1997 | Allen | 514/509 |
| 5,744,124 A | 4/1998 | Klokkers-Bethke et al. | |
| 5,989,529 A * | 11/1999 | Kaplan | 424/59 |
| 6,962,691 B1 * | 11/2005 | Lulla et al. | 424/45 |
| 8,147,872 B2 | 4/2012 | Crew et al. | |
| 2003/0095925 A1 | 5/2003 | Dugger, III | |
| 2004/0228883 A1 | 11/2004 | Karl | |
| 2005/0192210 A1 | 9/2005 | Rothbard et al. | |
| 2007/0053966 A1 * | 3/2007 | Ang et al. | 424/449 |
| 2007/0059346 A1 | 3/2007 | Maibach | |
| 2010/0016446 A1 * | 1/2010 | Gonda et al. | 514/742 |
| 2010/0184870 A1 * | 7/2010 | Groteluschen et al. | 514/742 |

FOREIGN PATENT DOCUMENTS

| | | | | |
|---|---|---|---|---|
| CA | 1718345 A1 * | 9/2009 | ............... | A61K 9/12 |
| CA | 2718345 | 9/2009 | | |
| DE | 3246081 A1 | 6/1984 | | |
| DE | 4038203 | 6/1992 | | |
| DE | 202008007318 U1 | 9/2008 | | |
| DE | 102008005484 A1 | 7/2009 | | |
| EP | 0448961 | 10/1991 | | |
| EP | 0461505 | 12/1991 | | |
| EP | 0471161 | 2/1992 | | |
| EP | 0448961 B1 * | 8/1995 | ............. | A61K 31/21 |
| EP | 1004294 A1 | 5/2000 | | |
| GB | 1205019 A | 9/1970 | | |
| RU | 2174838 C2 | 10/2001 | | |
| WO | 82/00005 A1 | 1/1982 | | |
| WO | 88/05306 | 7/1988 | | |
| WO | WO88/05306 * | 7/1988 | ............. | A61K 37/02 |
| WO | 96/27372 A1 | 9/1996 | | |
| WO | 97/38687 A1 | 10/1997 | | |
| WO | 99/17766 A1 | 4/1999 | | |
| WO | 99/38472 A2 | 8/1999 | | |
| WO | 01/43735 | 6/2001 | | |
| WO | 01/68062 A2 | 9/2001 | | |
| WO | 03/066472 A1 | 8/2003 | | |
| WO | 2004064779 | 8/2004 | | |
| WO | 2005/004989 A1 | 1/2005 | | |
| WO | 2005/107461 A2 | 11/2005 | | |
| WO | 2007/123955 A2 | 11/2007 | | |
| WO | 2009/092358 A1 | 7/2009 | | |
| WO | 2011/002606 | 1/2011 | | |

OTHER PUBLICATIONS

Sergio H. Ferreira et al., Blockade of hyperalgesia and neurogenic oedema by topical application of nitroglycerin, 1992, European Journal of Pharmacology, 217:207-209.*
Sergio H. Ferreira et al., "Blockade of hyperalgesia and neurogenic oedema by topical application of nitroglycerin," 1992, European Journal of Pharmacology, 217:207-209.*
Johns Hopkins Sports Medicine Patient Guide to Muscle Strain; date unavailable; Johns Hopkins Medicine, Orthopaedic Surgery [online], [retrieved Jan. 20, 2015], Retrieved from the Internet: <URL: http://www.hopkinsortho.org/muscle_strain.html).*
Definition of Bruise; 1996-2015, last editorial review Mar. 19, 2012; MedicineNet [online], [retrieved Jan. 20, 2015] Retrieved from the Internet: <URL: http://www.medicinenet.com/script/main/art.asp?articlekey=2541>.*
Edema, Dictionary.com [online], [retrieved Jun. 18, 2015] Retrieved from the Internet; <URL: http://dictionary.reference.com/browse/edema>.*
Fernandes et al., Involvement of guanylate cyclase and potassium channels on the delayed phase of mouse carrageenan-induced induced paw oedema; 2004; European Journal of Pharmacology, 501:209-214.*
Fernandes et al., Nitric oxide-induced inhibition of mouse paw edema: involvement of soluble guanylate cyclase and potassium channels; 2002; Inflammation Research, 51:377-384.*

(Continued)

*Primary Examiner* — Jane C Oswecki
(74) *Attorney, Agent, or Firm* — K&L Gates LLP

(57) ABSTRACT

Use of glyceryl trinitrate (GTN) for treating traumatic edemas.

15 Claims, No Drawings

(56) References Cited

OTHER PUBLICATIONS

Mense, "Muscle Pain: Mechanisms and Clinical Significance", Dtsch Arztebl Int, 2008, 105(12): 214-9.
Schranz et al., (1981), "Hemorrhagic pulmonary edema and cardiac failure following isolated head injury. Treatment with dobutamine and nitroglycerin," Monatsschr Kinderheilkd, 129 (4): 248-250. Abstract.
Kuroda et al., (1997), "Changes in cerebral blood flow accompanied with reduction of blood pressure treatment in patients with hypertensive intracerebral hemorrhages," Neurol Res., 19(2): 169-73. Abstract.
International Search Report for International Application No. PCT/EP2011/003890, Date of Mailing Nov. 11, 2011.
Written Opinion for International Application No. PCT/EP2011/003890, Date of Mailing Nov. 11, 2011.
Fernandes et al., (2004), "Involvement of guanylate cyclase and potassium channels on the delayed phase of mouse carrageenan-induced paw edema," European Journal of Pharmacology, Elsevier Science, NL, vol. 501, No. 1-3, pp. 209-214.
Bel Trame et al., (1998) "Nitrate therapy is an alternative to furosemidel morphine therapy in the management of acute cardiogenic pulmonary edema," Journal of Cardiac Failure, vol. 4, No. 4, pp. 271-279.
Molecularinfo.com reference [Retrieved on Dec. 1, 2010 from the Internet: <URL: http://www.molecularinfo.com/MTM/D/D3/D3-r/D3-4-60.html], 1 pg.
Nitrolingual Pumpspray product insert (nitroglycerin lingual spray), G. Pohl-Boskamp GmbH & Co. KG, Oct. 2008, 4 pgs.
Nitrolingual Pumpspray package labelling (nitroglycerin lingual spray), G. Pohl Boskamp GmbH & Co. KG, Nov. 2008, 1 pg.
Nitrolingual Pumpspray bottle labelling (nitroglycerin lingual spray), G. Pohl-Boskamp GmbH & Co. KG, May 2006, 2 pgs.
Scheife et al., Journal of Pharmaceutical Sciences, vol. 71, Issue 1, Abstract, 1982, 1 pg.
International Search Report for International Application No. PCT/EP2009/001772, Date of Mailing Jun. 16, 2009.
Written Opinion for International Application No. PCT/EP2009/001772, Date of Mailing Jun. 16, 2009.
International Search Report for International Application No. PCT/EP2012/000803, Date of Mailing Jun. 25, 2012.
Written Opinion for International Application No. PCT/EP2012/000803, Date of Mailing Jun. 25, 2012.

M. J. Pikal et al: "Vapor pressure of nitroglycerin in sublingual molded tablets: Implications for stability", Journal of Pharmaceutical Sciences, 1976, vol. 65, No. 9, pp. 1278-1284.
M. J. Pikal et al: "Polymer sorption of nitroglycerin and stability of molded nitroglycerin tablets in unit-dose packaging", Journal of Pharmaceutical Sciences, 1977, vol. 66, No. 9, pp. 1293-1297.
M. J. Pikal et al: "Effect of nitroglycerin-soluble additives on the stability of molded nitroglycerin tablets", Journal of Pharmaceutical Sciences, 1984, vol. 73, No. 11, pp. 1608-1612.
"Glyceryl Monostearate", In: R C Rowe. P J Sheskey. S C Owen: "Handbook of Pharmaceutical Excipients, 5th Edition", 2005, Pharmaceutical Press, London.
International Search Report for International Application No. PCT/EP2012/000802, Date of Mailing Jun. 6, 2012.
Written Opinion for International Application No. PCT/EP2012/000802, Date of Mailing Jun. 6, 2012.
"Barex Resins", INEOS Barex, USA, 2006, Retrieved from the Internet: URL:http://www.ineosbarex.com/files/upload/Ineos%20Barex%20Brochure.pdf, retrieved on May 15, 2012, the whole document.
Database Caplus [Online], Chemical Abstracts Service, Columbus, Ohio, US, 2004, Chen, Baoxi et al: "Effect of acrylonitrile-butadiene rubber on nitroglycerin migration from propellant to EPDM inhibitor", retrieved from STN, Database accession No. 2004:826842, abstract.
Daniel Banes: "Deterioration of nitroglycerin tablets", Journal of Pharmaceutical Sciences, vol. 57, No. 5, 1968, pp. 893-894.
European Search Report for EP12004187, Date of completion of search Sep. 28, 2012.
Cui X, et al., "Role of endothelial nitric oxide synthetase in arteriogenesis after stroke in mice", Neuroscience, New York, NY, US, vol. 159, No. 2, 2009, pp. 744-750.
Dinesh Kumar, et al., "Chronic sodium nitrite therapy augments ischemia-induced angiogenesis and arteriogenesis", Proceedings of the National Academy of Sciences, National Academy of Sciences, US, vol. 105, No. 21, 2008, pp. 7540-7545.
Hopkins et al., "Controlled delivery of vascular endothelial growth factor promotes neovascularization and maintains limb function in a rabbit model of ischemia", Journal of Vascular Surgery, C.V. Mosby Co., St Louis, MO, US, vol. 27, No. 5, 1998, pp. 886-895.
Persson et al., "Therapeutic arterigenesis in peripheral arterial disease: Combining Intervention and Passive Training", Vasa Journal for Vascular Diseases, vol. 40, No. 3, 2011, pp. 177-187.

* cited by examiner

USE OF GLYCERYL TRINITRATE FOR TREATING TRAUMATIC EDEMA

CROSS REFERENCE TO RELATED APPLICATIONS

This is the national phase under 35 U.S.C. §371 of International Application No. PCT/EP2011/003890, filed on Aug. 3, 2011, which claims priority to and the benefit of German Application No. 10 2010 033 182.1, filed on Aug. 3, 2010, the entire disclosures of each of which are incorporated by reference herein.

The present invention relates to the use of glyceryl trinitrate (GTN) for treating traumatic edema.

According to the present application the term "traumatic edema" is understood to mean the temporary occurrence of swelling conditions following bone fractures, contusions, sprains, dislocations, and burns. The traumatic edema is characterized by an instantaneous manifestation of the edema at the position of the trauma. It is caused by the rupturing of small lymph and blood vessels, which is discernible in the frequently concomitant hematoma. Often, traumatic edemas spontaneously disappear after a period of days to weeks. It is important to rapidly reduce traumatic edema in order alleviate pain, decrease complications of edema, and restore fitness for work. In addition, for bone fractures a required surgical procedure cannot be performed until swelling subsides at the fracture site.

Traumatic edema must be differentiated from posttraumatic, secondary lymphedemas, which are caused solely by a malfunction of the lymphatic system. They result from severe trauma with ruptures of great lymph channels or from the removal of lymphatic vessels caused by cancer surgeries. Furthermore, secondary lymphedema can result from radiation, chronic recurring inflammation of lymph channels or, in the tropic hemisphere, by parasitic diseases of the lymphatic system by filariae. Secondary posttraumatic lymphedemas heal only very slowly or not at all. Generally, lymph edemas display a normal skin colour and can easily be diagnosed.

During the healing phases of the hematomas accompanying the traumatic edemas, various skin discolorations occur due to breakdown of blood residues by the body. A distinction may be made among the following phases:
1. Red: Bursting of the capillaries, discharge of blood into the tissue
2. Dark reddish-blue: Blood clotting
3. Brownish-black: Enzymatic breakdown of hemoglobin to form choleglobin/verdoglobin
4. Dark green: Enzymatic breakdown of hemoglobin to form biliverdin
5. Yellowish-brown: Enzymatic breakdown of hemoglobin to form bilirubin Traumatic edema is currently treated by manual lymph drainage, compression, cooling, and elevation.

Glyceryl trinitrate (nitroglycerin), abbreviated below as GTN, is an active substance used for the treatment of angina pectoris, among other conditions. It is primarily used in emergency situations in the form of chewable capsules or as a sublingual spray, with the active substance penetrating the oral mucosa. Sublingual sprays are commercially marketed as propellant sprays and as pump sprays. Spray compositions containing propellants are disclosed, for example, in U.S. Pat. No. 3,155,574, European patent application EP 0 461 505, and German unexamined patent application DE 32 460 81. Propellant-free compositions containing GTN are described in European patent applications EP 0 448 961 and EP 0 471 161.

In addition, the effectiveness of transdermally administered GTN for treating Achilles tendinopathy is known. Paolini et al. (Paolini et al., The Journal of Bone and Joint Surgery, Volume 86/A, No. 5, 2004) report on the successful treatment of chronic noninsertional Achilles tendinopathy by topical administration of GTN. Gary J. McCleane describes in *Pain Management: Expanding the Pharmacological Options* (Wiley-Blackwell, 2008, Chapter 4) and in *Clinical Management of Bone and Joint Pain* (The Haworth Press, 2007, Chapter 5) the effective treatment of pain associated with various diseases of the musculoskeletal system, for example supraspinatus, extensor tendonitis, or osteoarthritis, by topical administration of GTN. Agrawal et al. (Agrawal et al., Diabetes Research and Clinical Practice, 77 (2007) 161-167) reports on the successful use of topically applied GTN for treating painful diabetic neuropathy. U.S. Pat. No. 5,698,589 discloses the effectiveness of topically applied GTN for treating male erectile dysfunction and female anorgasmia, and for assisting in wound healing of cuts. International patent application WO 2004/064779 reports on the treatment of nocturnal muscle cramps by topically applying GTN to the affected sites. Lastly, it is known from international patent application WO 01/43735 that topically applied GTN assists in the healing process of anal fissures.

Surprisingly, it has been found that topically applied GTN greatly accelerates the healing of traumatic edema. Traumatic edemas involved the temporary occurrence of swelling conditions following bone fractures, contusions, sprains, dislocations, impacts, blows or falls. In addition, traumatic edemas are characterized by closed or unbroken skin.

The composition used according to the invention contains GTN in addition to at least one excipient such as a solvent or a solid carrier, for example. The composition may optionally contain further excipients, for example penetration accelerators which promote transfer of the active substance into the damaged tissue, and preservatives and antioxidants which are able to prolong the shelf life of the composition, or, in the case of an aerosol or non-pump spray formulation, propellants which facilitate the application of the active substance.

Within the meaning of the invention, particularly suitable compositions are sprays which may be formulated as a propellant spray as well as propellant-free in the form of a pump spray. The compositions conveniently ensure the uniform application of a homogeneous active substance film to the affected sites on the skin. Gels or ointments, as well as transdermal systems such as patches, are also suitable.

The composition used is preferably topically applied to the affected areas of the skin.

It has been shown that single or multiple administration of a dose of 1.2 to 6 mg GTN on the day of injury, followed by daily application of 0.8 to 1.6 mg GTN, reduces and/or prevents the typical swelling and darkening of the affected skin sites and results in rapid healing of the injury. The detumescence of the swelling associated with a traumatic edema is accelerated; instead of darkening of the skin, the healing occurs with a green, followed by a yellow, coloration of the affected skin area. It has been determined that the individual healing phases are significantly shortened, and the overall healing period for the treated edemas is reduced by one-half, compared to an untreated edema.

Within the meaning of the invention, preferred GTN-containing propellant sprays contain, for 100 mg of the overall composition, 0.2 to 2.0 mg (0.2 to 2.0 percent by weight), preferably 0.2, 0.3, 0.4, 0.5, 0.6, 0.7, 0.8, 1.0, 1.2, 1.4, 1.6, or 1.8 mg GTN, 40 to 70 mg (40 to 70 percent by weight), preferably 45, 50, 55, 60, or 65 mg, propellant, and 30 to 60 mg (30 to 60 percent by weight), preferably 35, 40, 50, or 55 mg, of a suitable solvent. Preferred solvents in the propellant sprays are isopropanol, ethanol, n-pentane, propylene glycol, water, medium-chain triglycerides and mixtures thereof. As further additives, 0.01 to 2 mg (0.01 to 2 percent by weight) of a suitable preservative and/or fragrances or scents may be added to the composition. For example, n-butane, isobutane, and propane as well as mixtures thereof are suitable as propellants. Dimethyl ether and monochloroethane as well as noncombustible propellants such as hydrofluoroalkanes 1,1,1,2,3,3,3-heptafluoropropane (HFA 227) or 1,1,1,2-tetrafluoroethane (HFA 134a) may also be used.

Pump sprays preferred according to the invention comprise aqueous, oily or alcoholic solutions of the active substance, which in addition to 0.2 to 2.0, preferably 0.3 to 0.6, percent by weight GTN contain 30 to 50 percent by weight water, or 30 to 80 percent by weight of an alcoholic solvent. Preferred quantities of GTN in the pump sprays according to the invention are 0.2, 0.3, 0.4, 0.5, 0.6, 0.7, 0.8, 1.0, 1.2, 1.4, 1.6, or 1.8 percent by weight. Preferred quantities of water in the aqueous solutions are 35, 40, or 45 percent by weight, while preferred quantities of alcoholic solvents in the alcoholic solutions are 40, 50, 60 or 70 percent by weight. Further ingredients in aqueous solutions are alcoholic solvents, which are contained in a quantity of 20 to 70 percent by weight, preferably in a quantity of 30, 40, 50, or 60 percent by weight. The solutions may also contain 20 to 30 percent by weight, preferably 22, 24, 26, or 28 percent by weight, glycerol, 5 to 25 percent by weight, preferably 7, 9, 11, 13, 15, 17, 19, 21, or 23 percent by weight, propylene glycol, 5 to 25 percent by weight, preferably 8, 10, 12, 14, 16, 18, 20, 22, or 24 percent by weight medium-chain triglycerides (e.g., $C_6$-$C_{12}$ saturated fatty acid triglycerides), 5 to 15 percent by weight, preferably 6, 8, 10, 12, or 14 percent by weight triglycerol diisostearate, diethylene glycol monoethylether, or mixtures thereof, and 0.15 to 2.5 percent by weight menthol and/or eucalyptus oil. Suitable alcoholic solvents contain alcohols with 2 to 4 carbon atoms, ethanol and isopropanol or mixtures thereof being particularly suitable. In addition, the solutions can optionally contain a buffer, such as sodium lactate, disodium monohydrogen phosphate, sodium phosphate and calcium stearate in a quantity of less than 0.5% by weight as disclosed in U.S. Pat. No. 7,872,049.

Gels preferred for the use according to the invention contain 0.5 to 2 percent by weight, preferably 0.6, 0.8, 1.0, 1.2, 1.4, 1.6, or 1.8 percent by weight, GTN, 70 to 95 percent by weight, preferably 75, 80, or 90 percent by weight, of a medium-chain triglyceride marketed, for example, under the name Miglyol® 812, 2 to 6 percent by weight silica, 2 to 12 percent by weight ethanol, and optionally 0.01 to 2 percent by weight of a fragrance and/or scent.

A suitable ointment within the meaning of the invention contains 0.2 to 2.0 percent by weight, preferably 0.3, 0.4, 0.5, 0.6, 0.8, 1.0, 1.4, 1.6, or 1.8 percent by weight GTN, 2 to 10 percent by weight of a suitable medium-chain triglyceride (Miglyol® 812 or 840, for example), and 90 to 98 percent by weight of a water-free ointment base such as lanolin alcohol ointment, white Vaseline, or semisolid hard fat, for example.

For preparing the compositions according to the invention GTN is preferably used as stabilized concentrates in a liquid carrier such as propylene glycol or medium-chain triglycerides.

In some embodiments, a method is provided of accelerating healing of edema by contacting an external surface at the site of the edema with a composition that includes: glyceryl trinitrate in a quantity between about 0.2 percent by weight and about 2.0 percent by weight; a medium chain triglyceride and an alcohol, wherein the medium chain triglyceride and the alcohol are mixed in a ratio of about 10:90 to about 90:10; a component for enhancing penetration of the external surface by glyceryl trinitrate in a quantity between about 5.0 percent by weight and about 20 percent by weight; and, optionally, water. The external surface at the site of the edema is contacted with an amount of composition effective to accelerate healing of the edema when the skin at the external surface is unbroken. The composition can be in the form of a pump spray solution. The medium chain triglyceride can be a triglyceride of plant or semi-synthetic origin, a saturated C8 to C12 fatty acid triglyceride, a saturated C6 to C12 fatty acid triglyceride, or a combination of any two or more of the foregoing. In various embodiments, the alcohol is isopropanol and/or the component for enhancing penetration is triglyceroldiisostearate.

In some embodiments, a method is provided of accelerating healing of edema by contacting an external surface at the site of the edema with a composition that includes: glyceryl trinitrate in a quantity between about 0.2 percent by weight and about 2.0 percent by weight; at least one solvent; a component for enhancing penetration of the external surface by glyceryl trinitrate in a quantity between about 5.0 percent by weight and about 20 percent by weight; and, optionally, water. The external surface at the site of the edema is contacted with an amount of composition effective to accelerate healing of the edema when the skin at the external surface is unbroken. The composition can be in the form of a pump spray solution. In some embodiments, the solvent can be selected from propylene glycol, isopropanol, and combinations of the foregoing, and/or the component for enhancing penetration can be diethylene glycol monoethyl ether.

The compositions disclosed herein are useful for treating, alleviating and/or diminishing the formation of edemas, thereby resulting in significant acceleration of the corresponding healing process. Healing progress can be assessed by monitoring tissue volume, subcutaneous microcirculation (e.g., at a tissue depth of 2 mm to 8 mm), post capillary venous filling pressure, capillary blood flow, blood flow velocity, and oxygen saturation in the area of the affected tissue. These are characteristic data of the proportion of the local blood supply compared to the total volume and a proper means for describing venous stasis, ischemia and hyperemia.

Unless stated otherwise, percent by weight always refers to the weight of the composition.

The present invention is described in greater detail with reference to the following examples.

EXAMPLE 1

Propellant Spray

| Ingredient | Quantity in g |
|---|---|
| Propellant: Isobutane/n-butane/propane* | 50 |
| n-Pentane | 20 |
| Absolute ethanol | 29.4 |
| GTN | 0.6 |

*For example, in the following molar ratios: 14.83:29, 75:55.42

EXAMPLE 2

Propellant Spray

| Ingredient | Quantity in g |
|---|---|
| Propellant: Isobutane/n-butane/propane* | 70 |
| Absolute ethanol | 29.4 |
| GTN | 0.6 |

*For example, in the following molar ratios: 14.83:29, 75:55.42

EXAMPLE 3

Propellant Spray

| Ingredient | Quantity in g |
|---|---|
| Propellant: Isobutane/n-butane/propane* | 50 |
| Absolute ethanol | 49 |
| Menthol | 0.7 |
| GTN | 0.3 |

*For example, in the following molar ratios: 14.83:29, 75:55.42

EXAMPLE 4

Propellant Spray

| Ingredient | Quantity in g |
|---|---|
| Dimethyl ether | 50 |
| Water | 20 |
| Propylene glycol | 29.7 |
| GTN | 0.3 |

EXAMPLE 5

Propellant Spray

| Ingredient | Quantity in g |
|---|---|
| Monochloroethane | 50 |
| Eucalyptus oil | 0.5 |
| Absolute ethanol | 49.2 |
| GTN | 0.3 |

EXAMPLE 6

Propellant Spray

| Ingredient | Quantity in g |
|---|---|
| Propellant: n-butane/propane* | 50.0 |
| Isopropanol | 29.4 |
| Medium-chain triglycerides** | 20.0 |
| GTN | 0.6 |

*For example in the following molar ratios: 46.10:53.90
**Trade name: Miglyol ® 812

For preparation of the compositions according to Examples 1 through 6, the GTN was first dissolved in the respective solvents, while stirring. The additional excipients were then added, and the solution was stirred until homogeneous. The solution was filled into suitable containers which were then sealed. The pressure-liquefied propellants were then added via the valves.

EXAMPLE 7

Pump Spray

| Ingredient | Quantity in g |
|---|---|
| Water | 30 |
| Isopropanol | 32.4 |
| Eucalyptus oil | 2 |
| Absolute ethanol | 35 |
| GTN | 0.6 |

EXAMPLE 8

Pump Spray

| Ingredient | Quantity in g |
|---|---|
| Water | 45 |
| Absolute ethanol | 46 |
| Propylene glycol | 8 |
| Menthol | 0.5 |
| Eucalyptus oil | 0.2 |
| GTN | 0.3 |

EXAMPLE 9

Pump Spray

| Ingredient | Quantity in g |
|---|---|
| Medium-chain triglycerides* | 22.7 |
| Ethanol | 76 |
| Menthol | 0.7 |
| GTN | 0.6 |

*Trade name: Miglyol ® 812

EXAMPLE 10

Pump Spray

| Ingredient | Quantity in g |
|---|---|
| Water | 40 |
| Absolute ethanol | 31.45 |
| Menthol | 0.2 |
| Glycerol | 27.6 |
| Eucalyptus oil | 0.15 |
| GTN | 0.6 |

EXAMPLE 11

Pump Spray

| Ingredient | Quantity in g |
| --- | --- |
| Medium-chain triglycerides* | 19.4 |
| Isopropanol | 70 |
| Triglyceroldiisostearate | 10 |
| GTN | 0.6 |

*Trade name: Miglyol ® 812

EXAMPLE 12

Pump Spray

| Ingredient | Quantity in g |
| --- | --- |
| Propylene glycol | 21.4 |
| Isopropanol | 68 |
| Diethylene glycol monoethylether* | 10 |
| GTN | 0.6 |

*Trade name: Transcutol P

For preparation of the spray solutions according to Examples 7 through 12, the active substance was first dissolved in the solvent. The water and the other excipients were then added, and the solution was stirred until homogeneous. The solution was filled into suitable spray bottles.

EXAMPLE 13

Oleogel

| Ingredient | Quantity in g |
| --- | --- |
| Highly dispersed silica | 36.0 |
| Medium-chain triglycerides* | 794.0 |
| Absolute ethanol | 50.0 |
| Eucalyptus oil | 10.0 |
| GTN | 10.0 |

*Trade name: Miglyol ® 812

EXAMPLE 14

Ointment

| Ingredient | Quantity in g |
| --- | --- |
| GTN | 0.2 |
| Medium-chain triglycerides | 3.8 |
| Anhydrous ointment base** | 96.0 |

*Trade name: Miglyol ® 812
**For example, lanolin alcohol ointment, white Vaseline, or semisolid hard fat (Softisan ® 378, for example) may be used as bases.

EXAMPLE 15

A 30-year-old male patient with a fracture of the forearm, in which a hematoma associated with post-traumatic edema developed in the vicinity of the fracture site, was initially treated after immobilization of the arm on the affected area of the skin with 6 to 8 spray bursts, containing 100 mg each, of the formulation according to Example 9. The treatment was continued for 4 hours with administration of 3 to 4 spray bursts every 30 minutes, corresponding to an administered quantity of 1.8 to 2.4 mg GTN per application. The treatment was continued, including the second day after the start of treatment, with reduced frequency of application. It was observed that the dark blue coloration of the skin which usually occurs in hematomas was not present, and the traumatic swelling, which normally takes up to one week to subside, disappeared within two days, thus allowing an early surgical procedure on the fracture. The patient experienced no side effects, in particular no headaches.

Consequently, the topical administration of a composition containing GTN advantageously reduces the extend and degree of traumatic edema, reduces the period needed for the detumescence of a traumatic edema and a accompanying hematoma and thus effectively supports, e.g., the healing of a bone fracture, in so far as a necessary surgery be conducted at an earlier point of time. Since the typical coloration associated with a traumatic edema was not observed, moreover, an acceleration of biochemical processes associated with the formation and healing of a traumatic edema and a corresponding hematoma can be postulated.

EXAMPLE 16

Based on the preliminary clinical data an animal study will be performed to evaluate soft tissue restitution under topical application of GTN at a heavy soft tissue trauma using a rat model.

Both the clinical and the microcirculatory changes of soft tissue regeneration are examined, particularly with regard to post-traumatic edema and hematoma, after traumatic soft tissue injury. A standardized animal (rat) model of severe closed soft tissue injury is used. On the basis of this model new therapeutic options for soft tissue restitution after application of nitroglycerin and its effects on microcirculation of the skeletal muscle and the surrounding soft tissue after a severe closed soft tissue trauma can be evaluated.

The following observations are undertaken:
1. Clinical examination of soft tissue restitution, particularly with regard to the formation, and the healing of the traumatic edema and hematoma, under topical application of nitroglycerin after traumatization.
2. Characterization of the effect of the topical application of nitroglycerin after soft tissue traumatization on the microcirculation of the skin and the skeletal muscles with the aid of combined laser Doppler technique and tissue photospectrometry.

This study is performed in two phases. First, the effects of two different formulations containing the NO-donor nitroglycerin on microcirculation, particularly on the post-capillary venous filling pressure, in a tissue depth of 2 and 8 mm compared to a placebo solution are examined.

Second, the soft tissue restitution is evaluated after severe soft tissue trauma under standardized conditions. The healing processes of animals treated with a nitroglycerin formulation are compared to those treated with a placebo solution.

It is expected that topical application of nitroglycerin results in a positive effect on soft tissue restitution, particularly with respect to the formation and the healing of traumatic edemas and hematomas, resp. Without wishing to be bound by theory, such an effect could be explained by the vasodilatating properties of nitroglycerin and nitric oxide (NO), resp., e.g. by an increase of post-capillary venous drainage.

Study Design:

Both phases of the study are designed as experimental double-blind, placebo-controlled, and randomized investigations in an animal model.

The effect of a topically applied nitroglycerin formulation on the formation and healing of edemas and hematomas is investigated, and the microcirculation in a tissue depth of 2 mm and 8 mm of traumatized soft tissue of the lower leg of rats is compared to placebo. The primary endpoint is the evaluation of edema and hematoma of the lower leg of the rat by daily measuring the volume of the lower leg and by inspecting the leg visually over a period of 14 days after the injury. Moreover a daily photo documentation of the healing process is carried out.

As secondary endpoints the parameters of the microcirculation in 2 mm and 8 mm tissue depth are determined, these are the post capillary venous filling pressure, the capillary blood flow, the blood flow velocity, and the oxygen saturation of the tissue. These are characteristic data of the proportion of the local blood supply compared to the total volume and a proper means for describing venous stasis, ischemia and hyperemia. The dimensions of these parameters are defined as arbitrary units.

Study Medication:

Two nitroglycerin formulations and their respective placebo solutions serve as study medication. They are characterized as a non polar formulation according to example 11 and a more polar formulation according to example 12.

Animals:

Male Sprague-Dawley rats weighing between 250 and 300 g.

Measurement Device:

The microcirculation is determined in a non-invasive manner by the device Oxygen-to-see (O2C, LEA Medizintechnik, Gießen, Germany). This device combines the laser Doppler technique with tissue spectrophotometry and determines the relative blood flow, the blood flow velocity, the relative amount of hemoglobin, and the oxygen amount of the hemoglobin simultaneously in two tissue depths (2 and 8 mm) in real time.

Test Procedure:

After arrival the animals are acclimatized for 7 days prior to the study. Throughout the whole study the animals have unrestricted access to fresh water and dry food. A 12/12 hours light and darkness cycle is maintained. The animals are kept according to the appropriate guidelines. During examination the animals are anesthetized.

1. Study Phase

The animals are allocated to the trial medication and the treatment scheme in a randomized way. The treatment algorithm is based on Williams' square. In this design each treatment occurs only once in every sequence and in every period. In this order of treatments a possible period effect is balanced in an optimal manner. An exemplary design of the trial for four days is given in the following table:

| Sequence | Period | | | |
| --- | --- | --- | --- | --- |
| | day 1 | day 2 | day 3 | day 4 |
| 1 | A | B | C | D |
| 2 | B | D | A | C |
| 3 | C | A | D | B |
| 4 | D | C | B | A |

A Polar nitroglycerin preparation
B Non-polar nitroglycerin preparation
C Placebo of the polar preparation
D Placebo of the non-polar preparation The preparations are pipetted to the healthy skin of the left hind shank of the rats. At time 0 (before the application of the preparations) a baseline measurement is carried out followed by repeated measurements starting 30 seconds until 30 minutes after application. The microcirculation of the skin of the living rat is analysed using the Oxygen-to-see device (see above). Only one daily treatment with the preparations is carried out assuring a wash-out period of 24 hours. Thus any carry-over-effect can be excluded.

2. Study Phase
   1. Group: Control group, trauma, topical application of placebo, measurement of the microcirculation with the Oxygen-to-see device, clinical evaluation
   2. Group: Treatment group, trauma, topical application of nitroglycerin formulation, measurement of the microcirculation with the Oxygen-to-see device, clinical evaluation The animals are anesthetized and the left hind legs are shaved. The biometric data of the left shank are determined as baseline value for the clinical trauma evaluation. After fixation of the shank a baseline measurement of the microcirculation in the predefined area of the antero-lateral shank compartment for 2 minutes is carried out. After that a defined beat to the middle part of the antero-lateral compartment of the left shank is applied using the Controlled Impact Injury Technique with a gas-powered metal bolt (diameter: 1 cm, velocity 7 m/s, time of contact with the tissue: 1 s). A severe blunt, but closed tissue injury (no fracture, no perforation of the skin) is formed with this established method. Directly thereafter the measurement of the microcirculation with the Oxygen-to-see device is repeated for 5 minutes in all groups.

The test animals are set back to their cages and wake up from the narcosis. Three hours later the first clinical evaluation of the trauma is accomplished and the topical application of either the nitroglycerin formulation in the therapeutic group or placebo in the control group resp. to the traumatized area with a pump spray is carried out. The treatment is continued three times a day with three hour intervals for two weeks. Every day before the first treatment the extent of edemas and hematomas is documented by photography, the volume of the shank is examined by archimedic volumetry, the skin tolerance is evaluated, and the microcirculation is measured with the Oxygen-to-see device.

It is expected that the treatment of the animals with the compositions and methods of the present invention will alleviate and/or diminish the formation of a traumatic edema resulting in a significant acceleration of the corresponding healing process followed a traumatic edema and/or the corresponding hematoma. It is further expected that one or more of the clinical endpoints will be improved, thereby showing the effectiveness of the preparations.

The aspects, embodiments, features and examples of the invention are to be considered illustrative in all respects and are not intended to limit the invention, the scope of which is only defined by the claims. Other embodiments, modifications, and usages will be apparent to those skilled in the art without departing the spirit and the scope of the claimed invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise. As used herein, the term "about" refers to a ±10% variation from the nominal value, unless otherwise stated.

It should be understood that the order of steps or order for performing certain actions is immaterial so long as the present teachings remain operable. Moreover, two or more steps or actions may be conducted simultaneously.

Where a range or list of values is provided, each intervening integer and, where appropriate, decimal between the endpoints of that range or list of values is individually contemplated and is encompassed within the invention as if each value were specifically enumerated herein. In addition, smaller ranges between and including the endpoints of a given range are contemplated and encompassed within the invention. The listing of exemplary values or ranges is not a disclaimer of other values or ranges between and including the endpoints of a given range.

The invention claimed is:

1. A method of diminishing the formation of a traumatic edema comprising the step of:
applying topically to the traumatic edema about 1.2 to 6 mg glyceryl trinitrate, wherein the traumatic edema is caused by the rupturing of small lymph and blood vessels, and further wherein the volume of the traumatic edema measured by archimedic volumetry post injury is reduced as compared with an untreated traumatic edema.

2. The method of claim 1 further comprising applying to the traumatic edema, on a subsequent day, about 0.8 to 1.6 mg glyceryl trinitrate.

3. A method of diminishing the formation of a traumatic edema comprising the step of:
contacting a traumatic edema and an area adjacent to or in the vicinity of the traumatic edema with a composition comprising about 1.2 to 6 mg glyceryl trinitrate at about 0.2 to 2.0 percent by weight of glyceryl trinitrate in a suitable solvent, wherein the glyceryl trinitrate is administered topically, and wherein the traumatic edema is caused by the rupturing of small lymph and blood vessels, and further wherein the volume of the traumatic edema measured by archimedic volumetry post injury is reduced as compared with an untreated traumatic edema.

4. The method of claim 3 wherein the composition further comprises at least one excipient.

5. The method of claim 4 wherein the at least one excipient is selected from the group consisting of: medium-chain triglycerides, organic solvents, emulsifiers, water, propellants, preservatives, and penetration-assisting substances.

6. The method of claim 3 wherein the composition is in the form of a propellant spray or a pump spray.

7. The method of claim 6 wherein the composition is in the form of a propellant spray containing about 40 to 70 percent by weight of a propellant and about 30 to 60 percent by weight of a suitable solvent selected from the group consisting of: medium-chain triglycerides, water, ethanol, n-pentane, and propylene glycol, and mixtures thereof; in each case relative to the overall composition.

8. The method of claim 7 wherein the composition further comprises a fragrance.

9. The method of claim 3 wherein the composition is in the form of a pump spray further comprising about 30 to 50 percent by weight water and about 20 to 70 percent by weight of an alcoholic solvent; in each case relative to the overall composition.

10. The method of claim 3 wherein the composition further comprises about 20 to 30 percent by weight glycerol, about 5 to 10 percent by weight propylene glycol, and about 0.15 to 4 percent by weight fragrance; in each case relative to the overall composition.

11. The method of claim 3 wherein the composition further comprises about 30 to 80 percent by weight of isopropanol, about 5 to 25 percent by weight medium-chain triglycerides and about 5 to 15 percent by weight triglycerol diisostearate; in each case relative to the overall composition; and further wherein the composition is in the form of a pump spray.

12. The method of claim 3 wherein the composition further comprises about 30 to 80 percent by weight of isopropanol, about 5 to 25 percent by weight propylene glycol, and about 5 to 15 percent by weight diethylene glycol monoethylether; in each case relative to the overall composition; and further wherein the composition is in the form of a pump spray.

13. The method of claim 3 wherein the composition further comprises a buffer in a concentration of less than about 0.5 percent by weight; in each case relative to the overall composition.

14. The method of claim 1 or 3 further comprising the step of re-applying topically to the traumatic edema about 1.2 to 6 mg glyceryl trinitrate on the day of injury.

15. The method of claim 3 further comprising applying, on a subsequent day, about 0.8 to 1.6 mg glyceryl trinitrate.

* * * * *